United States Patent
Zhou

(10) Patent No.: US 9,664,625 B2
(45) Date of Patent: May 30, 2017

(54) INSPECTION OF SUBSTRATES USING CALIBRATION AND IMAGING

(71) Applicant: RUDOLPH TECHNOLOGIES, INC., Flanders, NJ (US)

(72) Inventor: Wei Zhou, St. Paul, MN (US)

(73) Assignee: Rudolph Technologies, Inc., Wilmington, MA (US)

( * ) Notice: Subject to any disclaimer, the term of this patent is extended or adjusted under 35 U.S.C. 154(b) by 0 days.

(21) Appl. No.: 14/432,045

(22) PCT Filed: Sep. 27, 2013

(86) PCT No.: PCT/US2013/062272
§ 371 (c)(1),
(2) Date: Mar. 27, 2015

(87) PCT Pub. No.: WO2014/052811
PCT Pub. Date: Apr. 3, 2014

(65) Prior Publication Data
US 2015/0253256 A1    Sep. 10, 2015

Related U.S. Application Data

(60) Provisional application No. 61/707,662, filed on Sep. 28, 2012.

(51) Int. Cl.
*G01N 21/00* (2006.01)
*G01N 21/88* (2006.01)
(Continued)

(52) U.S. Cl.
CPC ......... *G01N 21/8806* (2013.01); *G01B 11/02* (2013.01); *G01B 11/06* (2013.01);
(Continued)

(58) Field of Classification Search
CPC ........ G01F 23/00; G01N 21/00; G01N 23/00; G02B 5/00; G02B 21/00; G02B 17/00;
(Continued)

(56) References Cited

U.S. PATENT DOCUMENTS

| | | | | |
|---|---|---|---|---|
| 6,975,410 B1 * | 12/2005 | Sturgill | ................. | G01B 11/06 356/631 |
| 7,385,710 B1 * | 6/2008 | Sturgill | ................. | G01B 11/06 356/632 |

(Continued)

FOREIGN PATENT DOCUMENTS

| | | |
|---|---|---|
| JP | 2002-523763 | 7/2002 |
| JP | 2007-234685 | 9/2007 |
| TW | 201007116 A | 2/2010 |

OTHER PUBLICATIONS

PCT Search Report and Written Opinion for PCT/US2013/062272, mailed Jan. 21, 1014, 6 pages.

*Primary Examiner* — Tarifur Chowdhury
*Assistant Examiner* — Isiaka Akanbi
(74) *Attorney, Agent, or Firm* — Dicke, Billig & Czaja, PLLC

(57) ABSTRACT

An inspection system is disclosed. An optical assembly establishes an optical path between a light source and a detector. The optical assembly has a relatively large amount of longitudinal chromatic aberration, so that light at a first wavelength focuses on one region of a substrate in the optical path, while light at a second wavelength simultaneously focuses on another region of the substrate. The system can operate in a calibration mode to determine one or more wavelengths of light corresponding to regions of interest in the substrate and in an imaging mode to image regions of interest in the substrate.

16 Claims, 7 Drawing Sheets

(51) Int. Cl.
  *G01N 21/95*  (2006.01)
  *G01N 21/956*  (2006.01)
  *G01B 11/02*  (2006.01)
  *G01B 11/06*  (2006.01)

(52) U.S. Cl.
  CPC ... *G01N 21/9501* (2013.01); *G01N 21/95607* (2013.01); *G01N 2021/95615* (2013.01); *G01N 2201/02* (2013.01); *G01N 2201/062* (2013.01); *G01N 2201/10* (2013.01)

(58) Field of Classification Search
  CPC .. G01B 11/00; G03F 7/00; A61B 3/00; G11B 7/00; G03B 21/00; G01M 11/00
  USPC .............................. 356/399–401, 237.2–237.6
  See application file for complete search history.

(56) References Cited

U.S. PATENT DOCUMENTS

| | | | |
|---|---|---|---|
| 7,428,063 B2* | 9/2008 | Endo | G03F 7/70633 356/622 |
| 2002/0003626 A1* | 1/2002 | Fukui | G03F 7/70633 356/399 |
| 2002/0060793 A1* | 5/2002 | Fukui | G02B 7/28 356/400 |
| 2005/0146729 A1 | 7/2005 | Scheiner et al. | |
| 2006/0132806 A1 | 6/2006 | Shchegrov et al. | |
| 2007/0258084 A1* | 11/2007 | Fukui | G02B 21/247 356/123 |
| 2010/0182589 A1* | 7/2010 | Hirose | G01J 3/02 356/51 |
| 2011/0253671 A1 | 10/2011 | Lian et al. | |
| 2013/0021588 A1* | 1/2013 | Matsumoto | G01B 11/14 355/45 |

* cited by examiner

INSPECTION OF SUBSTRATES USING CALIBRATION AND IMAGING

CROSS-REFERENCE TO RELATED APPLICATIONS

This Utility Patent Application is a U.S. National Stage filing under 35 U.S.C. §371 of PCT/US2013/062272, filed Sep. 27, 2013, which claims the benefit of U.S. Provisional Patent Application No. 61/707,662, filed Sep. 28, 2012, incorporated by reference herein.

TECHNICAL FIELD

The present disclosure relates to inspection of semiconductor wafers.

BACKGROUND

Currently, inspection of semiconductor wafers involves illuminating one side of a semiconductor wafer, collecting reflected light from the one side, and analyzing the collected light for defects and for other criteria. While this works quite well for the one side, it provides no information about regions within the wafer or about an opposite side from the one side under inspection. Accordingly, there exists a need for an inspection system and method that can measure and inspect layers or regions of or within the wafer.

SUMMARY

One embodiment disclosed herein is a wafer inspection system. The wafer inspection system includes an optical system for directing light onto a wafer. The light has a spectrum that includes a plurality of wavelengths. During inspection, the optical system simultaneously focuses a first wavelength of light onto a first layer, volume or region of the wafer and focuses a second wavelength onto a second layer, volume or region of the wafer.

A further embodiment disclosed herein is a method of inspecting a wafer. The wafer includes one or more surfaces, layers, volumes or regions. The method includes focusing light at a first wavelength onto a first surface of the wafer. The method further includes focusing light having a second wavelength onto a second surface of the wafer.

BRIEF DESCRIPTION OF THE DRAWINGS

The foregoing and other objects, features and advantages disclosed herein will be apparent from the following description of particular embodiments disclosed herein, as illustrated in the accompanying drawings in which like reference characters refer to the same parts throughout the different views. The drawings are not necessarily to scale, emphasis instead being placed upon illustrating the principles disclosed herein.

DETAILED DESCRIPTION

Figure 1:
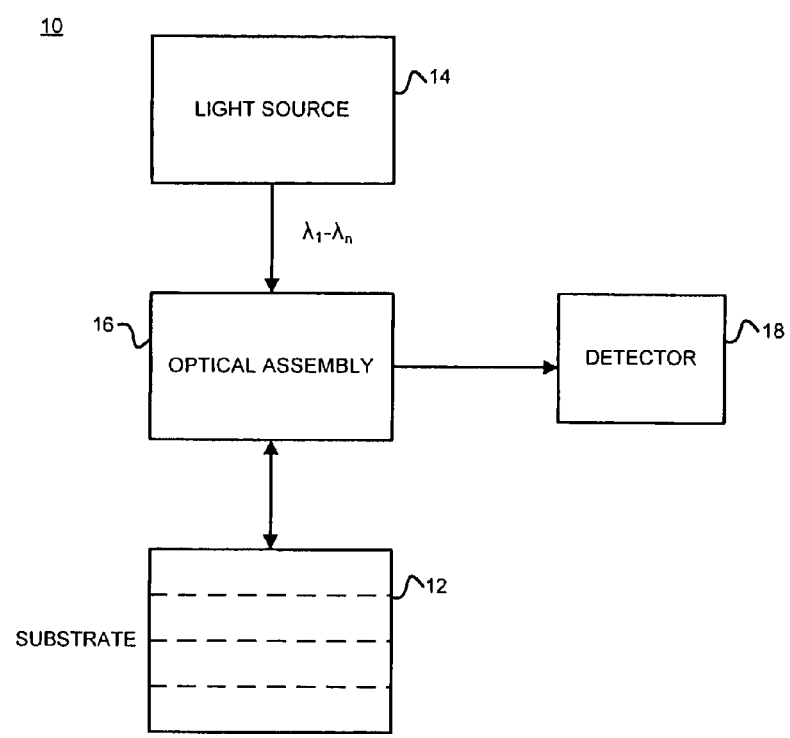
FIG. 1 is a schematic drawing of an example inspection system.

FIG. 1 is a side-view schematic drawing of an exemplary optical system 10 for inspection of a substrate 12 such as a wafer. There are various quantities that can be inspected/measured with the present system 10. One quantity is inspection of structures, intended (e.g., parts of a semiconductor device) or unintended (e.g., defects such as chips, cracks, scratches or particles), on or in the substrate 12 under test or inspection. One such intended structure is a via formed into or through a semiconductor substrate 12. Another quantity is alignment of structures formed on one or more semiconductor substrates 12. Alignment can be performed in a spot scanning chromatic confocal arrangement with infrared (IR) light being focused furthest from the imager and shorter wavelengths being focused closer to the imager. A third quantity is wafer thickness, which can include a profile of a wafer at various positions or over substantially its entire surface.

Substrate 12 can be formed of one or more different features such as layers and/or structures formed on or within the substrate 12. Example substrates include a semiconductor wafer, a stacked wafer, a die, a stacked die, embedded wafer level ball grid array (eWLB) substrate, gallium arsenide substrate, etc. Although schematically illustrated as having a plurality of layers, substrate 12 can be formed of a single layer. Features on substrate 12 may include, but are not limited to, silicon layers, oxide layers, dielectric layers, metal layers, polymer layers, bond pads, alignment features, high aspect ratio vias, through silicon vias (TSV), resist layers, passivation layers, active circuits, bumps, and remaining silicon thickness (RST), also known as wafer overburden. It should be noted that these features include etched structures that accommodate features that are positioned on a substrate 12. In one example, the etched structures include a bare or partially processed wafer having a TSV formed therein prior to filling the TSV with conductive material.

With particular reference to inspection of a substrate 12 that is a semiconductor wafer, it is worth nothing that a semiconductor wafer has a characteristic bandgap, which determines a characteristic wavelength at which the wafer transitions between being optically opaque and transparent. The bandgap depends only on the material or materials from which the wafer is formed. For instance, silicon has a bandgap of about 1.1 eV (electron volts), which corresponds to a characteristic wavelength of about 1.13 μm (micrometers). A silicon wafer is generally transparent for wavelengths greater than this characteristic wavelength, and generally opaque for wavelengths shorter than the characteristic wavelength. Silicon is generally considered transparent at a near-infrared wavelength of 1.2 μm, opaque for wavelengths in the visible spectrum between 0.4 μm and 0.7 μm, and opaque for near-infrared wavelengths between 0.7

μm to about 1.1 μm. In addition to pure silicon and compounds thereof, the present system 10 may have application in inspecting substrates 12 made with gallium, arsenic, boron, indium, cadmium, zinc, copper, lead, tin, bismuth, titanium, uranium, barium, lanthanum, mercury, platinum, silver, iron and selenium and compounds thereof.

In performing thickness measurement, the present optical system 10 uses a near-infrared wavelength to reflect off a bottom surface of the wafer, and simultaneously uses a visible wavelength to reflect off a top surface of the wafer. In situations where the characteristic bandgap is known for substrate 12, the near-infrared wavelength can be selected based on the characteristic bandgap (i.e., greater that a corresponding characteristic wavelength). By collecting light from the two reflections simultaneously, the optical system may obtain thickness information, both an average thickness and thickness variations over a surface of the wafer. The optical system 10 may also obtain alignment information for particular features on top and bottom surfaces of the wafer. In addition, the optical system 10 may also inspect the top and bottom surfaces of the wafer simultaneously for defects. In further embodiments, multiple layers and features can be detected using light of three, four, five or more wavelengths to separately delineate layers of substrate 12.

Regardless of the particular structure of substrate 12, a light source 14 provides light having at least two wavelengths to the substrate 12. The wavelengths are denoted as $\lambda_1$-$\lambda_n$ in FIG. 1 and are ultimately directed onto substrate 12 along an optical axis. As referenced herein, the optical axis can be referred to as the Z-axis, where an XY position is within a plane perpendicular to the Z-axis and substantially parallel with a top surface of substrate 12. The following paragraphs describe how such light can be produced and how it can be delivered to the wafer.

Light source 14 can be a single source, such as a broadband, white-light light emitting diode (LED), or multiple sources, with each source covering a different part of the electromagnetic spectrum. In some cases, the light source 14 includes a near-infrared light source such as a dedicated LED (i.e., a non-broadband LED) having a center wavelength in the infrared, such as 1.2 μm. The light source 14 may also include a visible light source such as a broadband LED (e.g., a white-light LED), that has an emission spectrum that spans across a range of visible wavelengths. In other cases, the light source 14 can include an incandescent light bulb, or other suitable filament-based light source. In effect, any broadband or essentially monochromatic source or combination of sources such as xenon, halogen, incandescent, LED, arc lights or the like may be used as well.

Figure 2A:
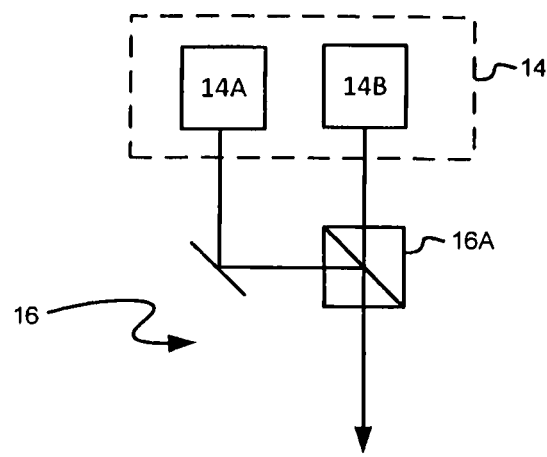
FIG. 2A is a schematic drawing of multiple light sources combined using a beam splitter.
Figure 2B:
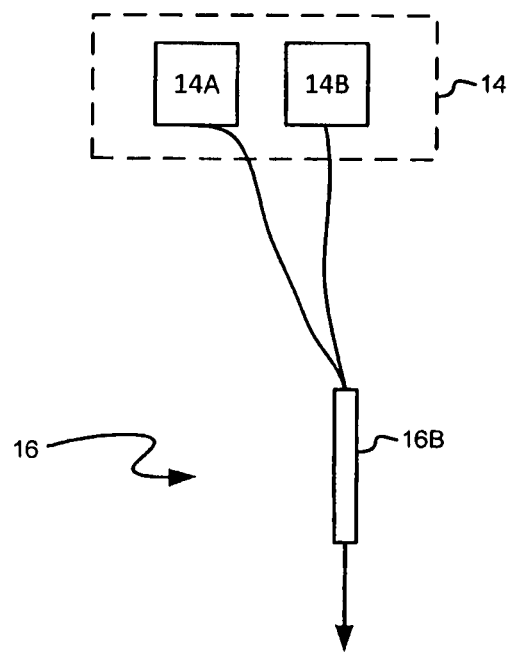
FIG. 2B is a schematic drawing of multiple light sources combined using optical fiber.

Once the light including multiple wavelengths $\lambda_1$-$\lambda_n$ is produced by light source 14, it is directed toward the substrate 12. Light from source 14 may travel toward the substrate through the air, through optical fiber or through a liquid light guide. Where source 14 includes a single emitter of broadband light, this light is emitted directly toward the substrate. Where multiple emitters of light are used as part of source 14, these multiple sources may be combined onto a single optical path using an optical assembly 16 that includes one or more optical elements. For example, as illustrated in FIG. 2A, wherein the light source includes a first source 14A and a second source 14B, the optical assembly 16 can include a wavelength-sensitive beamsplitter 16A positioned at an oblique angle of incidence, such as 45 degrees. Light having a wavelength below a certain cutoff wavelength is transmitted (or reflected) by the beamsplitter 16A, while light having a wavelength above the cutoff wavelength is reflected (or transmitted). Such beamsplitters are known in the art, and may be formed as plates, as cubes, or in any other suitable shape. In an alternative embodiment, light from sources 14A and 14B is conducted by optical fiber to a coupler 16B, as illustrated in FIG. 2B.

The optical assembly 16 can further include one or more lenses, for example a collimating lens and/or an objective lens for directing light onto the substrate 12 along an optical axis. Delivery of light to the one or more lenses from light source 14 can be through free space, such as propagation in air, or through a coupler such as an optical fiber or a bundle of optical fibers as illustrated in FIG. 2B. For fiber delivery, the delivery end of the fiber or fiber bundle can be placed at a predetermined distance away from the one or more lenses with the one or more lenses receiving light emerging from the bundle. Alternatively, an end of a fiber bundle or an end of a coupler may emit light in the direction of the substrate 12 directly.

In one embodiment, an objective lens that focuses light onto the substrate 12 can be selected to generate a particular amount of chromatic aberration. Optical materials, such as typical glasses and plastics, have a characteristic refractive index, which is a measure of how fast light travels in the particular material. In most or all known glass and plastics, the refractive index varies as a function of wavelength. The variation in refractive index with wavelength is expressed numerically as a quantity known as dispersion. If one forms lenses or lens elements from curved pieces of these glasses or plastics, one finds that the focal lengths vary with refractive index, due to the non-zero dispersion of the corresponding glass or plastic materials. For example, a typical bi-convex lens will have a higher refractive index at shorter wavelengths, and will have a higher power and therefore a shorter focal length at shorter wavelengths. This variation in focal length or position, as function of wavelength, is known as chromatic aberration. Examples of various optical systems which embody chromatic aberration as a means for measuring surface topography are given in U.S. Pat. No. 5,790,242 to Stern, et al., which patent is hereby incorporated by reference in its entirety.

In one embodiment, the objective lens in system 10 described herein can be deliberately selected to include a relatively large value of chromatic aberration. Due to this large chromatic aberration, light of a first wavelength (e.g., visible light) can come to focus at one surface or region of substrate 12 (e.g., the top of the wafer), while light of a second wavelength focuses at a different surface or region of substrate 12 (e.g., the bottom of the wafer or a top surface of a subsequent wafer), which is substantially disposed away from the focus plane of the first wavelength. In one embodiment, visible light is used to measure and/or image a top surface of the wafer, while simultaneously infrared light is used to measure and/or image the bottom of the wafer. By forming multiple images simultaneously, or in rapid succession without moving any optical elements, the system 10 may gather more information than a comparable system that has optical elements on both sides of the wafer. In an alternative embodiment, the wavelengths of light need not be transmitted through the objective lens simultaneously, but performed in a sequential manner. In any event, inspection can be conducted for a single distance between the objective lens and substrate 12, without the need to scan (e.g., mechanically) the objective lens along the optical axis.

Light reflected from substrate 12 is provided to a detector 18, which can include one or more sensors as desired. The detector 18 can be coupled to a processor, computer or the like (not shown) to analyze the light received by the detector

18. In one embodiment, the detector 18 can be a spectrometer using a grating or other device to separate light into constituent parts, a sensor (e.g., a camera) using a wavelength specific filter, or one or more sensors using a wavelength specific beamsplitter, etc. such that only selected wavelengths are analyzed. In one particular example, the detector 18 can include a hot mirror and cold mirror to direct received light to a silicon camera (generally in the visible light ranges) and infrared camera (generally in the infrared light ranges), respectively. In a further embodiment, a spectrometer is used to resolve intensity peaks in light received at the detector 18.

Detector 18 may be formed using standard CMOS (complementary metal-oxide semiconductor) or CCD (charged coupled device) type sensors or cameras. These types of sensors are often sensitive to IR wavelengths of about 800 nm (nanometers) to about 1000 nm, but this sensitivity tends to drop off above this range of wavelengths. Using longer IR wavelengths above about 1000 nm improves the ability of system 10 to peer through or into substrates formed of materials such as silicon, but necessitates the use of sensors sensitive to these longer wavelengths such as those made from gallium arsenide and the like. Unfortunately, while gallium arsenide type sensors are more sensitive to IR wavelengths, they are less sensitive to light in the visible wavelengths. In some cases, a CCD or CMOS camera is used that has at least residual sensitivity at ranges approaching 1000 nm (more likely in range from about 750/800 nm to 1000 nm). Such a camera will also then be sensitive to shorter, visible wavelengths. The chromatic aberration is sufficient to focus at least one of the present wavelengths at a top surface of a full wafer and at a bottom surface, respectively. The chromatic aberration along with the wavelengths present in the light source 14 will span the thickness of a one full wafer plus a preferably, but not necessarily required, additional fraction of a wafer thickness. For typical silicon wafers, a full thickness wafer is about 0.75 mm thick for a 300 mm diameter wafer and is about 1 mm for a 450 mm diameter wafer.

As discussed in more detail below, system 10 is operable in a calibration mode and an imaging mode. The optical assembly 16 establishes an optical path from the light source 14 to the detector 18 to evaluate characteristics of the substrate 12. In the calibration mode, system 10 operates using confocal principles to determine one or more positions of interest in the substrate 12. In one embodiment, the calibration mode involves a pair of conjugate apertures positioned along the optical path and configured to focus one or more wavelengths of light onto positions of interest within the wafer. For example, the calibration mode can determine topography and/or thickness of the substrate 12. In the imaging mode, one or both of the pair of apertures are removed from the optical path. In one embodiment, the one or more apertures can be coupled with an actuator or other suitable mechanism configured to move the apertures between a first position in the optical path and a second position removed from the optical path. Removing said one or both apertures allows a broader region of the wafer to be imaged such that inspection of the substrate 12 can be performed. In one example, the detector 18 can capture images simultaneously of both an upper and lower surface of the substrate 12.

Figure 3A:
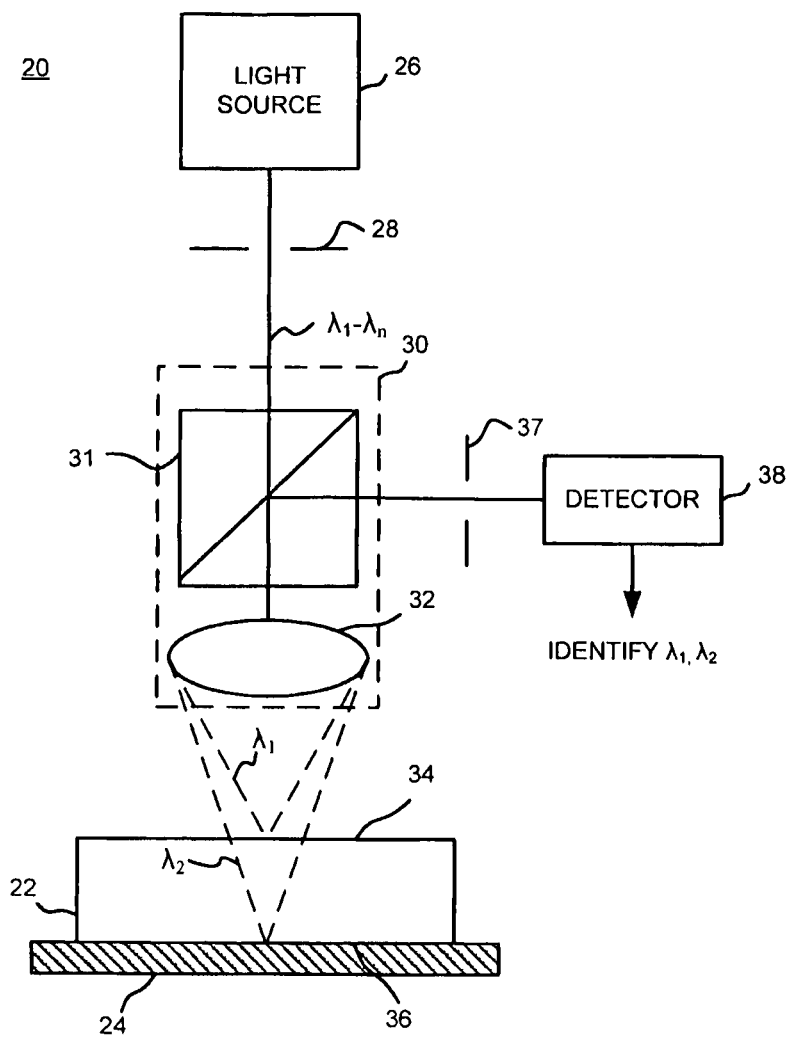
FIG. 3A is a schematic drawing of a representative implementation of the inspection system of FIG. 1 for measuring thickness of a wafer in a calibration mode.

With the above principles in mind, FIG. 3A is a schematic drawing of an example chromatic confocal inspection system 20 implementing concepts presented above with respect to FIG. 1 for measuring a wafer 22 supported on a stage 24. Using system 20, it can be determined which wavelengths of light are correlated to positions of interest in the wafer 22 (e.g., top, bottom, TSV depth). System 20 can also perform confocal thickness and topography inspection/metrology in discrete, selectable operational modes. In system 20, a spot or slit scanning system is used to generate a 2D/3D image of a wafer 22 that is under inspection. By scanning one or more apertures or slits over a 2D surface that is under inspection using stage 24, one may obtain chromatically encoded profile or height information about the wafer 22 at the scanned locations. In any event, system 20 is equipped to provide relative movement between wafer 22 and system 20 (e.g., using stage 24) to different XY positions so as to inspect a desired portion of wafer 22.

Light originates from a light source 26, with light having at least wavelengths $\lambda_1$ and $\lambda_2$. Light at the two wavelengths $\lambda_1$, $\lambda_2$ is combined into a single path, passes through an aperture 28, and into an optical assembly 30, which herein includes a beamsplitter 31 and an objective lens 32. Optical assembly 30 is but one example assembly and can include one or more lenses, beamsplitters or any other suitable optical element or combination of optical elements. Aperture 28 can, for example, be a pinhole aperture or a slit forming a line scanning mechanism. The objective lens 32 has a relatively large amount of longitudinal chromatic aberration, which directs and substantially focuses one wavelength $\lambda_1$ onto a top surface 34 of the wafer 22 and the other wavelength $\lambda_2$ onto the bottom surface 36 of the wafer 22. The objective lens 32 collects the reflected light from the wafer, reflects the light through beamsplitter 31, an aperture or slit 37 and onto a detector 38. Aperture 37 operates in an optically conjugate plane with aperture 28 to provide focused light to detector 38.

Using the optical arrangements described above, it is possible to determine a wafer thickness. In one embodiment, a near-infrared wavelength $\lambda_2$ (e.g., approximately 1.2 μm) readily transmits through the wafer 22, and is brought to focus on the bottom 36 of the wafer. Simultaneously, because of the chromatic aberration of lens 32 (or optical assembly 30), a shorter wavelength $\lambda_1$ is brought to focus at a particular plane away from the bottom surface 36 of the wafer, toward the top surface 34 of the wafer 22. In some embodiments this plane is the upper surface of the wafer 22. Using the detector 38, wavelength $\lambda_1$ that focuses on the top surface 34 can be resolved or decoded (e.g., by color parsing, spectrometry), while wavelength $\lambda_2$ that focuses on the bottom surface 36 can be similarly resolved and the relative positions that correlate to the wavelengths $\lambda_1$ and $\lambda_2$ may be determined. Where detector 38 includes a spectrometer, peaks in light sensed by detector 38 can identify $\lambda_1$ and $\lambda_2$ and the respective distances that correlate thereto.

During the calibration mode, the intensity detected at selected wavelengths can be compared with a threshold or expected value to determine characteristics of the area under observation. For example, if $\lambda_1$ and $\lambda_2$ are equal to or approximately the expected value, the thickness of the wafer 22 at the area under observation would be the calculated thickness as determined in the calibration mode. On the other hand, if intensity of $\lambda_1$, $\lambda_2$ or both wavelengths are not the expected value, a defect or other structure can be presumed at the area under observation.

In another embodiment that does not utilize a spectrometer as part of detector 38, the system 20 may include a wavelength-sensitive filter 40 (FIG. 3B), such as a bandpass filter, to select the particular wavelength that is, as a result of the chromatic aberration of lens 32, brought to focus at a selected surface, region, or layer of the wafer 22. The wavelength-sensitive filter may be positioned in an incident path (i.e., prior to objective lens 32), a return path (i.e., after reflection from wafer 22), or both. By changing the filter to pass different wavelengths, one may select a different vertical position (surface, region or layer) within or on the wafer 22 at which light is focused. By including filter(s) 40 in a changeable carrier such as a filter wheel or turret (not shown), one may successively switch between multiple wavelengths $\lambda_1$-$\lambda_n$.

In any event, subtracting the positions obtained from decoding the wavelengths $\lambda_2$ from $\lambda_1$ can provide a thickness measurement for wafer 22. Calculation of thickness is dependent upon an amount of chromatic aberration of optical assembly 30. Regarding the objective lens 32, it can be desirable to exaggerate the longitudinal chromatic aberration while compressing the transverse chromatic aberration. This arrangement reduces the change in lateral magnification for different wafer thicknesses.

Note that the depth of focus per wavelength for the objective lens 32 correlates to a resolution in wafer thickness that may be measured. A smaller depth of focus may require a larger numerical aperture for the objective lens 32, which may in turn produce a larger magnification for the inspection system 20. This situation may strain the existing throughput capabilities of the system 20 as with an increase in magnification typically results in a smaller field of view. Performing an inspection at only one wavelength or a narrow wavelength band may force longer exposure times for existing cameras. For these reasons, in some cases, in may be desirable to use a Time Delay Integration (TDI) camera with a direct current (DC) (not strobe or pulsed) light source, which may improve system throughput and may increase the signal-to-noise ratio of the system.

In one embodiment, system 20 can operate in both a calibration mode and an imaging mode. In the calibration mode, a plurality of different wavelengths of light are sent along an incident path from light source 26, though aperture 28, beamsplitter 31 and to objective lens 32. Objective lens 32 focuses the light along the optical axis at a particular XY position on wafer 22, as dictated by the chromatic aberration of the lens 32. The identity of wavelengths $\lambda_1$ and $\lambda_2$ are then determined for the particular XY position (e.g., by using a spectrometer, other wavelength sensitive sensors, sensor arrangements), which can then be used to calculate thickness of wafer 22. Stage 24 can then be used to move wafer 22 to a plurality of other XY positions for wafer 22. At each XY position, the thickness can be recorded. Based on these thickness measurements (i.e., obtained by calculating a difference between identified wavelengths producing peaks), various flatness specifications of the wafer 22 can be calculated. As implied, "flatness specifications" provide an indication of planarity for wafer 22, which can be calculated on a global or local scale. These specifications include topography of both an upper and lower surface bow, warp, total thickness variations, total indicated reading (the difference between maximum and minimum calculations), spherical reference measurement, local focal plane deviation (deviation of one surface when the other surface is assumed flat), local thickness variations, etc.

As part of the calibration mode, two or more wavelengths can be selected to inspect wafer 22 in the imaging mode. In imaging mode, correlation of wavelength to vertical position of the wafer 22 is used to select which positions of the wafer 22 are imaged. Captured images can be compared images to other images, to threshold(s) or to models, piecewise or by the entire image. In performing this comparison, characteristics of the wafer 22 can be identified. Example inspection techniques are further disclosed in U.S. Pat. No. 6,826,298, the contents of which are hereby incorporated by reference in its entirety. Captured images can further be used for alignment, where relative positions of features identified in multiple captured images can be determined and evaluated.

Figure 3B:
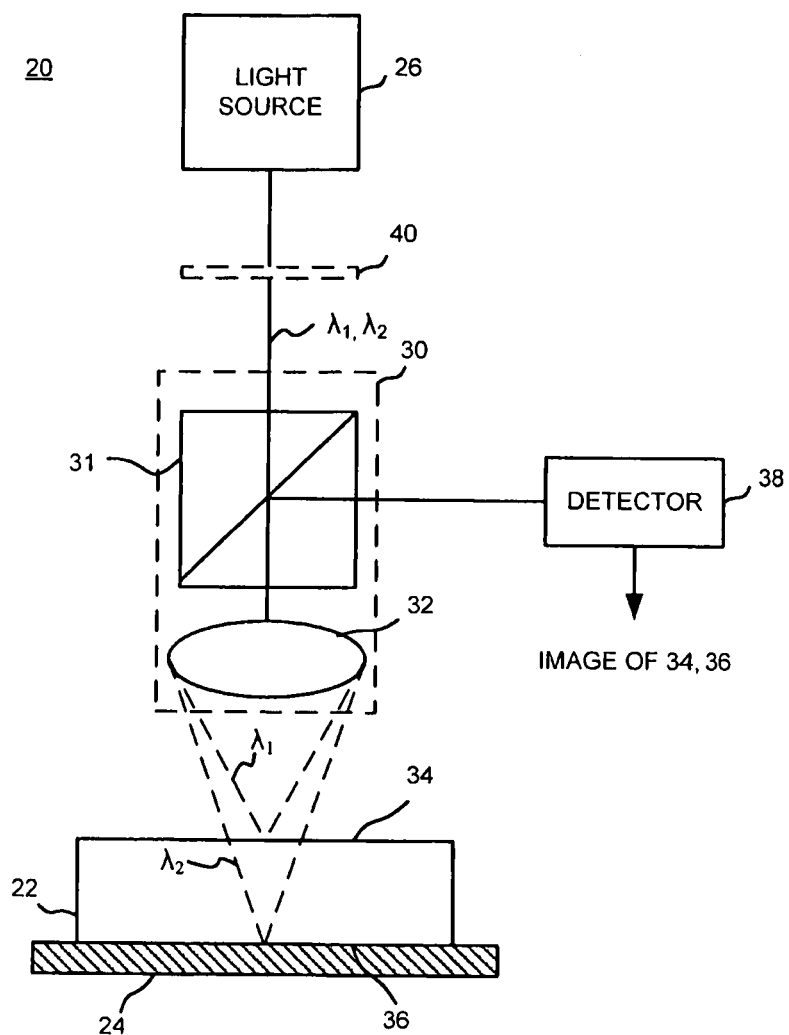
FIG. 3B is a schematic drawing of another representative implementation of the inspection system of FIG. 1 for inspection in an imaging mode.

An example of a system 20 arranged in an imaging mode is schematically illustrated in FIG. 3B. To convert the system 20 between calibration and imaging modes, one or both of the apertures 28, 37 are removed from an optical path of system 20. This converts the system 20 from one that operates on a confocal principle to one that can capture images of an area of a wafer 22. The determination of which apertures 28 and/or 37 are to be removed is dependent upon an optical design selected for optical assembly 30. The apertures 28, 37 can be coupled with an actuator or other mechanism (not shown) that removes the apertures 28, 37 from the optical path of system 20.

System 20, in its imaging mode, is capable of capturing 2D images of a wafer 22. Inspection in the imaging mode can therefore be performed for a broader XY area of wafer 22 and preferably for substantially all of wafer 22. Since system 20 retains lens 32 when in its imaging mode, a suitably arranged detector may simultaneously capture images of multiple vertically separated selected surfaces, layers or regions, each such position being selected by using a wavelength identified using the calibration mode of the system 20. Optical assembly 30, being subject to chromatic aberration, focuses discrete wavelengths as discrete positions along the optical axis within and on the wafer 22. One or more sensors in detector 38 are arranged to capture an image at the discrete wavelengths and accordingly at the discrete positions within or on the wafer 22.

Figure 4A:
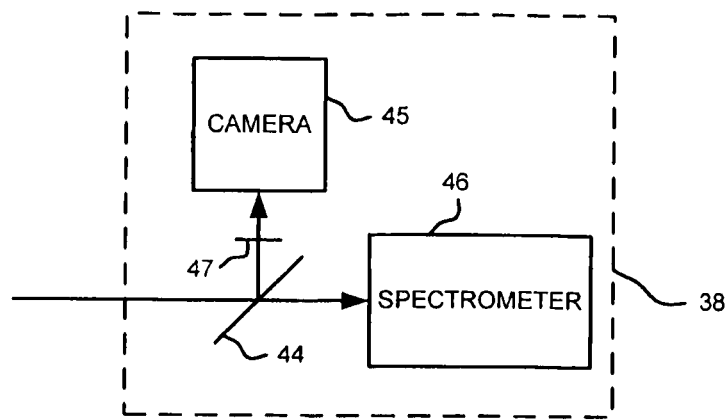
FIG. 4A is a schematic drawing of an example detector employing a camera and a spectrometer.
Figure 4B:
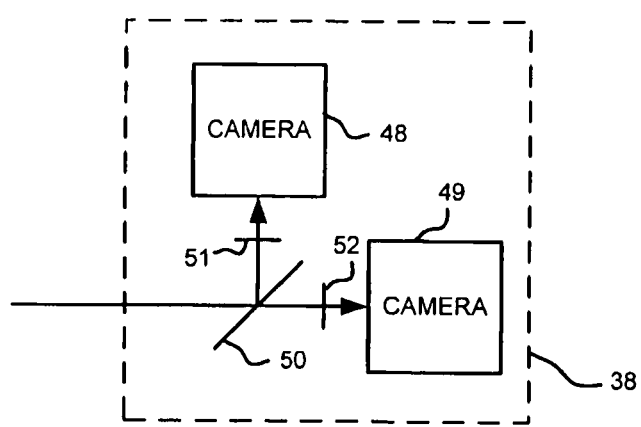
FIG. 4B is a schematic drawings of an example detector employing multiple cameras.

FIGS. 4A and 4B illustrate two example implementations of detector 38. In FIG. 4A, a beamsplitter 44 directs light to a monochrome camera 45 and a spectrometer 46. The monochrome camera 45 is sensitive to the entire range of visible light and at least some IR. A bandgap filter 47 directs selected light to the camera 45 to capture images at selected vertical positions on or within the wafer 22. Spectrometer 46 detects intensity at wavelengths provided to the detector 38. In FIG. 4B, the spectrometer is not shown, but movable with respect to first and second monochrome cameras 48 and 49 in order for system 20 to operate in the calibration mode. The cameras 48 and 49 receive light from a beamsplitter 50 and corresponding filters 51 and 52. The filters 51 and 52 limit respective cameras 48 and 49 to sensing selected wavelengths. Changing filters 51 and 52 can change the selected wavelengths received by cameras 48 and 49 and the position within or on the wafer that is imaged.

In an embodiment where two wavelengths are selected (e.g., one for a top surface and one for a bottom surface of wafer 22) inspection of the wafer 22 in the imaging mode can be provided quickly and over a larger area than the calibration mode. In an alternative embodiment, three or more wavelengths can be selected for the imaging mode as desired. One approach to selecting the desired wavelengths is to use one or more wavelength specific filters 40. Where a filter 40 that passes a given wavelength is utilized, an image of the wafer 22 at the vertical position of the wafer 22 that corresponds to the given wavelength may be obtained. Changing the filter 40 as by the use of a filter wheel or turret (not shown) allows one to select other discrete vertical positions on or within the wafer 22 for imaging. Note that the use of a filter 40 allows the use of a monochrome sensor that is sensitive to a range of wavelengths, including the selected wavelength, as a detector 38. Detector 38 can successively record the intensity of light received at the selected wavelengths $\lambda_1$, $\lambda_2$ and form images of the surfaces that correspond to each of the wavelengths. As seen in FIG. 3B, wavelengths $\lambda_1$ and $\lambda_2$ that correspond to a top surface 34 and a bottom surface 36 of the wafer 22 are selected. One who is skilled in the art will appreciate that other wavelengths and hence surfaces can be selected.

Figure 5:
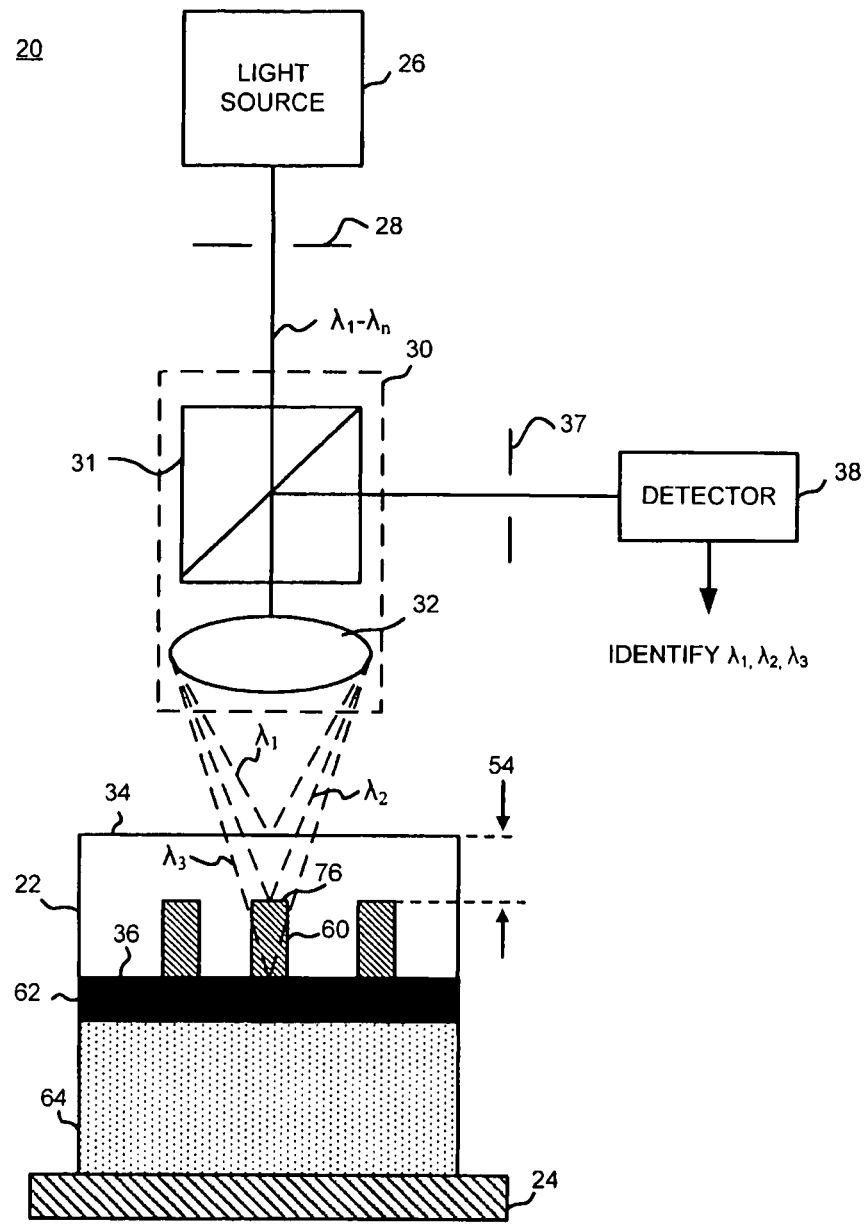
FIG. 5 is a schematic drawing of the implementation of FIG. 3A for measuring remaining silicon thickness and through silicon vias.

In addition to measuring wafer thickness using concepts presented herein, further features for measurement include remaining silicon thickness (RST) and through silicon vias (TSVs). FIG. 5 is a schematic diagram of system 20 in the calibration mode for inspecting RST 54 and TSVs in the wafer 22. The RST 54 is defined as the remaining silicon between a via bottom 76 and the bottom surface 34 of wafer 22 during the manufacture of 3D integrated circuits (3DICS) and TSVs. As shown in FIG. 5, the wafer 22 has the top surface 34 and bottom surface 36 as previously discussed, a TSV 60 extending into the wafer 22, an adhesive layer 62 and a carrier 64. The carrier 64 is coupled to the translation stage 24 for moving the wafer 22 relative to system 20.

Using system 20 in the calibration mode can quickly determine distances to various features on and within wafer 22. If detector 38 includes a spectrometer, peaks of wavelengths correspond to different vertical positions in the wafer 22. To calculate thickness of the wafer 22, peaks occur in the output of the spectrometer occur at the top surface 34 and bottom surface 36 of the wafer 22. When optical assembly 30 is in a position above a TSV 60, peaks in the output of the spectrometer will occur at the top surface 34 and at an intermediate position within the wafer 22. In a bare or partially processed wafer 22, a peak can also occur at the bottom surface 36. In any event, RST 54 can be calculated based on the difference between the top surface 34 and the intermediate position. The optical assembly 30 can be scanned over the entire wafer 22 or portions thereof. If positions of the TSVs within wafer 22 are known, RST thickness measurement can be performed for one, multiple or all TSVs.

To measure RST 54 and TSVs 60, light from the light source 26 passes through the aperture 28, beamsplitter 31 and is focused by the objective lens 32 onto wafer 22. A first wavelength of light $\lambda_1$ is reflected off the top surface 34, a second wavelength of light $\lambda_2$ is reflected off of surface 76 of TSV 60 and a third wavelength of light $\lambda_3$ is reflected off the bottom surface 36. $\lambda_1$, $\lambda_2$ and $\lambda_3$ can be identified by detector 38 as discussed above. Once wavelengths, $\lambda_1$, $\lambda_2$ and $\lambda_3$ are identified, RST 54 can be calculated by decoding $\lambda_1$, $\lambda_2$ and $\lambda_3$ and subtracting $\lambda_2$ from $\lambda_1$, where thickness of wafer 22 can be calculated by decoding $\lambda_1$, $\lambda_2$ and $\lambda_3$ and subtracting $\lambda_3$ from $\lambda_1$. Once the wavelengths are identified in the calibration mode, system 20 can be operated in the imaging mode to further inspect wafer 22, TSV 60, layer 62, carrier 64 and/or combinations thereof.

In the event via 60 is not transparent to wavelength $\lambda_3$, RST 54 can be calculated for the XY position directly above via 60. Subsequently, translation stage 24 can move wafer 22 to a subsequent XY position such that via 60 does not interfere with wavelength $\lambda_3$ from reaching bottom surface 36.

In an alternative embodiment, inspection of wafer 22 can be performed from a reverse side of wafer 22, for example through stage 24, carrier 64 and adhesive layer 62. In such an embodiment, thickness of carrier 64 and adhesive layers 62 can be calculated as discussed above. Additionally, presence of vias 60 can also be calculated. Additionally, multiple systems 20 can be used, one directed at the top surface 34 and one positioned below the stage 24 and directed at the carrier 64.

Figure 6:
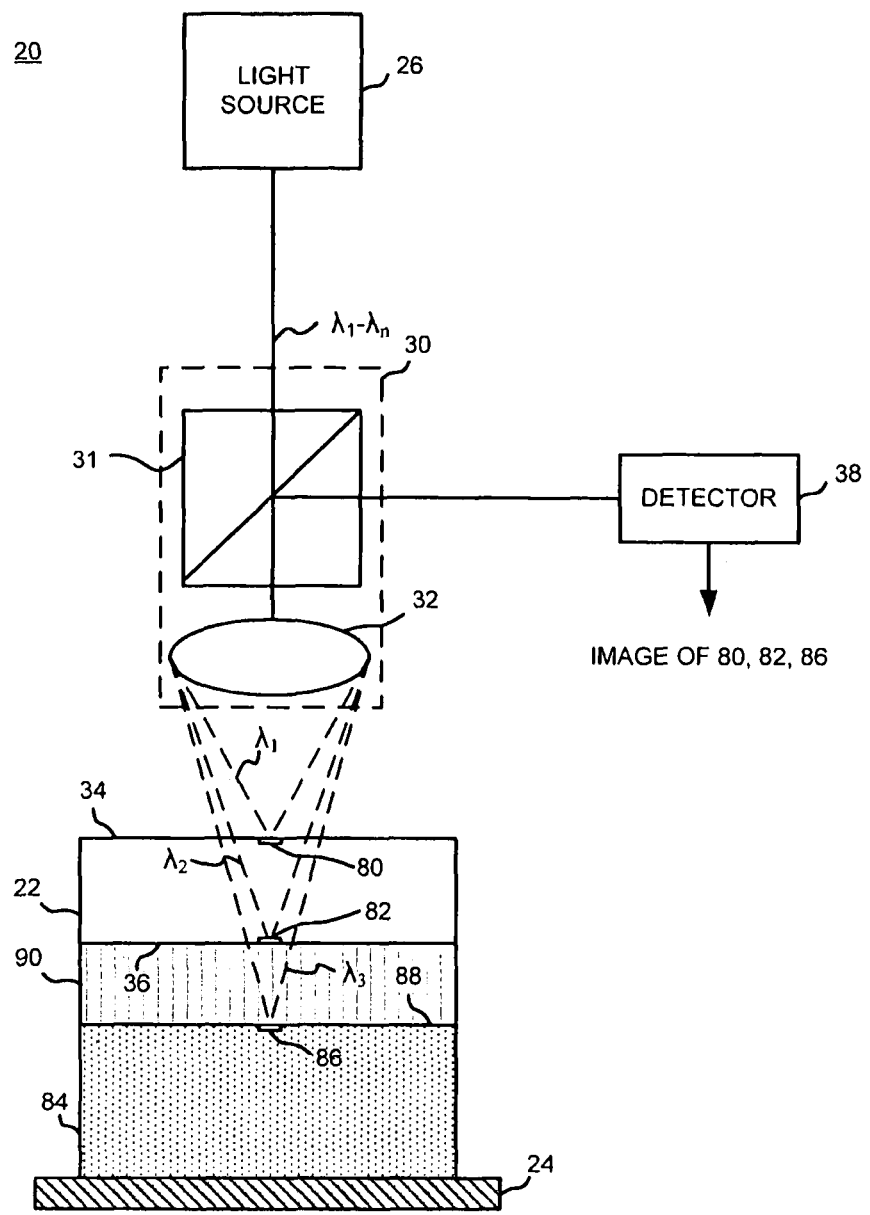
FIG. 6 is a schematic drawing of the implementation of FIG. 3B for evaluating alignment of structures.

FIG. 6 is an implementation of system 20 for aligning structures on one or more substrates in the imaging mode. As illustrated, wafer 22 includes a first alignment structure 80 positioned at top surface 34 and a second alignment structure 82 positioned at bottom surface 36. Additionally, a second wafer 84 is positioned on stage 24 and includes an alignment structure 86 positioned on its top surface 88, with an adhesive layer 90 between wafers 22 and 84. During inspection, detector 38 can form an image of alignment structures 80, 82 and 86 to determine a relative position of wafer 84 with respect to wafer 22. This information can be useful in evaluating bonding between wafer 22 and wafer 84. For example, if structures 80, 82 and 86 are aligned, it can be determined that bonding has been performed adequately.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An optical system, comprising:
a light source;
a detector positioned to receive light from the light source and determine intensity of received light at selected wavelengths;
an optical assembly positioned to establish an optical path from the light source to the detector;
a pair of apertures conjugate to one another and positioned in the optical path; and an actuator coupled to at least one of the pair of apertures, the actuator configured to move the at least one of the pair of apertures into and out of the optical path;
wherein the optical system is configured to operate in a calibration mode and an imaging mode, the imaging mode having at least one of the pair of apertures removed from the optical path;
wherein detector includes a first module for performing the calibration mode and a second module apart from the first module for performing the imaging mode.

2. The optical system of claim 1, where the calibration mode allows the detector to simultaneously determine topography of an upper surface of a substrate and a thickness of the substrate.

3. The optical system of claim 1 wherein the imaging mode allows the detector to capture an image of an upper surface of a substrate and an image of a bottom surface of the substrate simultaneously.

4. The optical system of claim 1 wherein the imaging mode includes both apertures removed from the optical path.

5. The optical system of claim 1, wherein the light source generates light with at least one wavelength in the visible spectrum and at least one wavelength that is near infrared.

6. The optical system of claim 1, wherein the detector is sensitive to visible light and to near infrared light.

7. The optical system of claim 1, wherein the first module includes a monochrome camera and the second module includes a spectrometer.

8. The optical system of claim 1, wherein the optical assembly includes an objective lens with chromatic aberration sufficient to focus light from the light source onto a first surface and a second surface of a wafer.

9. A wafer inspection system operable in a calibration mode and an imaging mode, comprising:
- a light source configured to generate light having a plurality of wavelengths;
- an optical assembly positioned to direct light from the light source onto the wafer, the optical assembly including an objective lens with chromatic aberration sufficient to focus light from the light source onto a first surface and a second surface of the wafer;
- a detector positioned to receive light from the optical assembly;
- wherein in the calibration mode, the detector determines a first wavelength of light in the visible light spectrum that substantially corresponds to the first surface and a second wavelength of light in the near infrared light spectrum that substantially corresponds to the second surface, and
- further wherein in the imaging mode, the detector forms an image of the first surface and an image of the second surface.

10. The wafer inspection system of claim 9, wherein the detector includes a first module for performing the calibration mode and a second module apart from the first module for performing the imaging mode.

11. A method, comprising:
- establishing an optical path from a light source to a detector;
- determining a first wavelength that substantially corresponds to a first region of a substrate positioned along the optical path;
- determining a second wavelength that substantially corresponds to a second region of the substrate;
- based at least in part on a characterization of the chromatic aberration of a lens that directs light onto the substrate, determining a distance between the first and second surfaces.

12. The method of claim 11 wherein the distance is one of a wafer thickness and a remaining silicon thickness.

13. The method of claim 11 further comprising:
- removing an aperture from the optical path;
- capturing simultaneously an image at the first wavelength and an image at the second wavelength.

14. The method of claim 13, wherein the aperture is movable into and out of the optical path, and further wherein the steps of determining a first wavelength and determining a second wavelength include the aperture inserted into the optical path, and even further wherein the step of capturing includes the aperture removed from the optical path.

15. The method of claim 11, wherein the first wavelength is in the visible light spectrum and the second wavelength is in the near infrared light spectrum.

16. The method of claim 11, wherein the substrate is a wafer having opposing, first and second major outer surfaces, and further wherein the step of determining determines the distance between the first and second major outer surfaces.

* * * * *